US006447997B1

(12) United States Patent
Los et al.

(10) Patent No.: US 6,447,997 B1
(45) Date of Patent: Sep. 10, 2002

(54) GENE CODING FOR GADD153 AS A CLINICAL DIAGNOSTIC AND PROGNOSTIC IN CANCER THERAPY

(75) Inventors: Gerrit Los, San Diego, CA (US); Dennis P Gately, Elkins Park, PA (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 08/896,406

(22) Filed: Jul. 18, 1997

(51) Int. Cl.[7] .......................... C12Q 1/68; C07H 21/04
(52) U.S. Cl. ........................................ 435/6; 536/23.5
(58) Field of Search ..................... 435/6, 91.2; 536/23.5

(56) References Cited

U.S. PATENT DOCUMENTS 5,885,786 A * 3/1999 Cabot ........................ 435/7.21

OTHER PUBLICATIONS

Los, G. et al. Proc. Annu. Meet. Am. Assoc. Cancer Res. 37:A939, Mar. 1996.*
Los, G. et al. Proc. Annu. Meet. Am. Assoc. Cancer Res. 35:A3277, Mar. 1994.*
de las Alas, M. et al. Proc. Am. Clin. Oncol. 15:A571, May 1996.*
Mileo, A.M. et al. Anticancer Res. 10(4):903–6, 1990.*
Spencer, C.M. et al. Drugs 48(5):794–847, Nov. 1994.*

* cited by examiner

*Primary Examiner*—W. Gary Jones
*Assistant Examiner*—Diana Johannsen
(74) *Attorney, Agent, or Firm*—Benjimin Aaron Adler

(57) ABSTRACT

The GADD153 gene is used herein as a molecular marker for in vivo tumor cell injury which occurs in response to chemotherapy. A GADD153-based prognostic method for tumor clinical response in a patient undergoing chemotherapy is provided. By determination of the magnitude of increase, above baseline, in GADD153 mRNA in a sample derived from a tumor in a patient after administration of a chemotherapeutic agent, the method is able to predict the tumor clinical response and, thus, the patient therapeutic response. This method is advantageous over known prognostic methods for tumor clinical response in that it can accurately and rapidly predict therapeutic responses including tumor progression, partial regression and complete regression for a wide range of tumors and chemotherapeutic agents.

5 Claims, 12 Drawing Sheets

SEQUENCE LISTING

<160> NUMBER OF SEQ ID NOS: 4

<210> SEQ ID NO 1
<211> LENGTH: 15
<212> TYPE: DNA
<213> ORGANISM: Mus musculus

<400> SEQUENCE: 1
catacatcac cacac                                                    15

<210> SEQ ID NO 2
<211> LENGTH: 15
<212> TYPE: DNA
<213> ORGANISM: Mus musculus

<400> SEQUENCE: 2
tgaccactct gtttc                                                    15

<210> SEQ ID NO 3
<211> LENGTH: 24
<212> TYPE: DNA
<213> ORGANISM: Mus musculus

<400> SEQUENCE: 3
gagcgggaaa tcgtgcgtga catt                                          24

<210> SEQ ID NO 4
<211> LENGTH: 24
<212> TYPE: DNA
<213> ORGANISM: Mus musculus

<400> SEQUENCE: 4
gatggagttg aaggtagttt cgtg                                          24

GENE CODING FOR GADD153 AS A CLINICAL DIAGNOSTIC AND PROGNOSTIC IN CANCER THERAPY

The government owns rights in the present invention pursuant to grant number CA 67269-01 from NIH, the National Institutes of Health.

FIELD OF THE INVENTION

The present invention relates generally to the fields of cancer and chemotherapy and more particularly, to the field of diagnostic and prognostic methods for the same. The invention provides a method that analyzes the relative amount of GADD153, as a function of the magnitude of the increase in GADD153 expression following DNA damage, as a clinical tool in monitoring and detectng tumor damage in response to a chemotherapeutic agent or other anti-cancer treatment.

BACKGROUND OF THE INVENTION

The accurate quantitation of the extent of tumor injury in patients as a result of treatment is often a problem. Normally, the effectiveness of chemotherapy or radiation therapy cannot be determined for at least several weeks and often longer. This presents an obstacle to improving the management of cancer patients particularly when alternative therapeutic modalities are available. Quantitation of molecular events occurring in response to injury in the tumor in vivo following cytotoxic injury may permit more rapid assessment of the likelihood of response (20,21).

Cells cope with injury by changing their pattern of gene expression, and some of these same changes occur in common in different types of cells. Transcription of the proto-oncogenes, c-fos and c-jun, for example, is rapidly induced by exposure to a wide variety of exogenous stimuli including, cytotoxic agents (1,2,3). The expression of these "early response genes" results in the rapid induction of many other genes, primarily regulated at the level of transcription (4,5). Holbrook et al. reported the isolation of a DNA damage-inducible gene, GADD153, from hamster (6) and human cells (7). GADD153 was one of 5 different genes found to be coordinately induced by either growth arrest or agents that cause DNA damage (8). They demonstrated that the GADD153 promotor was responsive to a broad spectrum of genotoxic agents, and subsequent work has provided evidence that the activation of the GADD153 promotor occurred as a direct result of DNA damage.

Elucidation of the molecular processes involved in the cellular injury response is yielding opportunities for the identification of novel markers that reflect the extent of injury produced in tumors by treatment with chemotherapeutic agents (23). Work in laboratories has identified GADD153 as an important player in the cellular injury response.

GADD153 is a gene that is strongly transcriptionally activated by cDDP (11,24) as well as by other types of cellular stress (25), including other classes of chemotherapeutic drugs (10,26). Among the genes whose message levels are known to increase following cellular injury, GADD153 is of particular interest as a potential marker because of the magnitude of its induction.

The GADD153 gene is unique in that it is not responsive to TPA despite the presence of an AP-1 binding site, distinguishing itself from other response genes such as the "early response" gene, C-JUN, and heat shock family genes. However, GADD153 can undergo inducible phosphorylation on two adjacent serine residues by a specific stress activated MAP kinase (29) which enhances the ability of GADD153 to function as a transcriptional activator (29). Prior observations of the present inventors showed that GADD153 is functionally located downstream of a hypothetical injury detection site as shown by the induction kinetics of GADD153, but upstream of the cell cycle control and cell growth events (23,29). GADD153 may serve as a link between early and late events in the response to cellular damage. However, its specific use as a marker for the extent of the cellular injury response has not been proposed nor tested.

In comparison to many other genotoxic agents and treatments, cDDP causes an unusually rapid activation of the GADD153 promotor (10). The mechanism responsible for the activation of GADD153 expression following DNA damage is still unclear.

Although other diagnostic and prognostic methods for tumor response to clinical therapy exist, none have found broad application due to their inherent limitations. The need remains for an improved prognostic and/or diagnostic method for tumor clinical response to chemotherapy.

SUMMARY OF THE INVENTION

Data by the present inventors demonstrate that GADD153 is induced by DNA damage in a dose dependent manner. In one aspect, the present invention provides a method for predicting a patient's therapeutic response to chemotherapy. In one embodiment, the method provides a GADD153 mRNA-based prognostic method for assessing clinical response by a tumor to chemotherapeutic agent. The present method is advantageously much more rapid than known prognostic methods, and requires only minimal invasion of a patient. The present method accurately predicts tumor clinical response to chemotherapeutic agents and can be used to predict tumor progression or partial as well as complete regression after treatment with a chemotherapeutic agent, through assessment of the magnitude of increase in GADD153 mRNA present in a sample derived from the tumor.

Accordingly, in some embodiments, the present invention provides a prognostic method for clinical response by a tumor to a chemotherapeutic agent comprising: administering a chemotherapeutic agent to a patient having a tumor; and determining the magnitude of increase above a control baseline for GADD153 mRNA in a sample derived from said tumor a period of time after administration of said chemotherapeutic agent; said magnitude of increase above baseline in GADD153 mRNA being predictive of a clinical response by said tumor.

In yet another aspect, the invention provides a prognostic method wherein a tumor biopsy is used to assess relative GADD153 mRNA levels in a subject having been treated with a chemotherapeutic agent.

In some embodiments, determination of the magnitude of increase, above baseline, in GADD153 mRNA is done during one or more of various time periods following administration of a chemotherapeutic agent. It is contemplated that the best time periods after administration of the chemotherapeutic agent for determination of the magnitude of increase above baseline, in GADD153 mRNA can vary according to the tumor being treated and the chemotherapeutic agent being used. Specifically, the determination of the magnitude of increase, above baseline, in GADD153 mRNA in a sample derived from a tumor can be done about 6 to about 72 hours after administration of a chemotherapeutic agent.

The magnitude of increase in GADD153 mRNA in a sample derived from a tumor treated with a chemotherapeutic agent will be determined relative to the expected or observed magnitude of increase, i.e. the baseline, in a sample derived from the same tumor but not treated with the chemotherapeutic agent. Generally regarding the therapeutic benefit received by a tumor-bearing patient undergoing chemotherapy, the larger the observed magnitude of increase in GADD153 mRNA, the greater the therapeutic benefit received by the patient.

In some embodiments, where the tumor is a head or neck carcinoma, and the chemotherapeutic agent being used includes cisplatin, the magnitude of increase, above baseline, in GADD153 mRNA in the range of less than about 7-fold indicates a tumor clinical response of tumor progression. In another embodiment, the magnitude of increase, above baseline, in GADD153 mRNA is in the range of greater than or equal to about 1 to less than or equal to about 2-fold, the tumor clinical response indicated is partial regression. In yet another embodiment, where the magnitude of increase, above baseline, in GADD153 mRNA is in the range of greater than about 2-fold, the tumor clinical response indicated is regression. It is contemplated that the limits for magnitude of increase, above baseline, in GADD153 mRNA can overlap while still providing an accurate prognostic method.

It is contemplated that the present methods can be applied in vivo, ex vivo and/or in vitro with a wide range of tumors in mammals. A broad range of chemotherapeutic agents and tumor types are contemplated by the invention as well.

In another embodiment, the present invention provides that changes in GADD153 mRNA may be quantitatively linked to the extent of tumor cell kill in vitro. In yet another embodiment, changes in GADD153 mRNA are quantitatively limited to the dose of chemotherapeutic agent, using cells grown as xenografts in vivo. In a further embodiment, the invention provides that the magnitude of increase in GADD153 mRNA level be measured after administration of cisplatin and that the level indicated is correlatable to the tumor clinical response in a patient with advanced head and/or neck carcinoma.

Yet another embodiment of the invention provides a method whereby the magnitude of increase in GADD153 mRNA measured after administration of paclitaxel or progesterone in combination with paclitaxal is correlatable to the tumor clinical response in the tumor-bearing patient.

Another aspect of the invention provides a screening method for the detection of tumor clinical response to chemotherapy. Thus, the invention also provides a GADD153 mRNA-based diagnostic method for tumors. This aspect of the invention is particularly advantageous over known diagnostic methods, as it provides rapid and accurate diagnostic information for a broad range of tumors. Accordingly, this aspect of the invention provides a GADD153 mRNA-based prognostic method for tumor clinical response to a chemotherapeutic agent comprising administering a chemotherapeutic agent to a patient having a tumor; and determining the magnitude of increase above baseline in GADD153 mRNA in a sample derived from said tumor a period of time after administration of said chemotherapeutic agent; said magnitude of increase above baseline in GADD153 mRNA being predictive of a clinical response by said tumor.

In some embodiments, the magnitude of increase above baseline, in GADD153 mRNA in a sample derived from the tumor is done about 12 to about 48 hours after administration of the chemotherapeutic agent, or in some uses, between about 12 to about 48, or about 24 hours, after administration of the chemotherapeutic agent. Based on the magnitude of difference in GADD153 mRNA observed, the clinical response indicated by use of the particular chemotherapeutic agent is tumor progression, partial tumor regression or complete tumor regression.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Following long-standing patent law convention, the terms "a" and "an" mean "one or more" when used in this application, including the claims.

As used herein, the term "tumor" means both benign and malignant cancers, tumors or neoplasms, and includes melanomas, lymphomas, leukemias, and sarcomas. Illustrative examples of tumor tissues are cutaneous tumors, such as malignant melanomas and mycosis fungoides; hematologic tumors such as leukemias, for example, acute lymphoblastic, promyelocytic, acute myelocytic or chronic myelocytic leukemia; lymphomas, such as Hodgkin's disease or malignant lymphoma; gynecologic tumors, such as ovarian and uterine tumors; urologic tumors, such as those of the prostate, bladder or testis; soft tissue sarcomas, osseous or non-osseous sarcomas, breast tumors; tumors of the pituitary, thyroid and adrenal cortex; gastrointestinal tumors, such as those of the esophagus, stomach, intestine and colon; pancreatic and hepatic tumors; laryngeal papillometastases and lung tumors; and squamous cell carcinomas of the head and neck.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Table 1 lists the sequences that are referenced throughout the following examples.

ing concentrations of cDDP was observed. Over a greater than 2 log range of tumor cell kill, the correlation coefficient was 0.98.

Figure 4A:
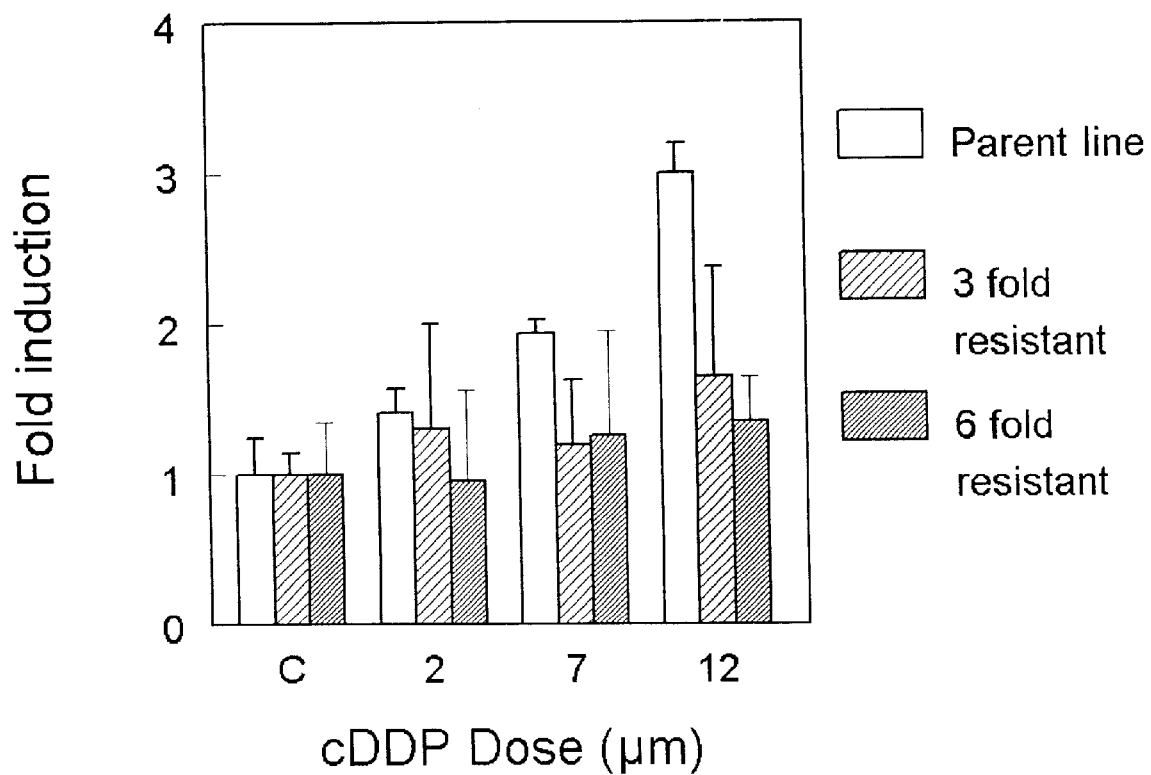
FIGS. 4a and 4b. Magnitude of increase in GADD153 mRNA level in cDDP-sensitive and resistant variants of UMSCC10b cells after exposure equimolar concentrations of cDDP (FIG. 4a) and after exposure to equitoxic concentrations of cDDP (FIG. 4b) Error bars, ±SD.

Without being held to a particular mechanism of action, the present inventors believe that the magnitude of increase in GADD153 mRNA level reflects the extent of tumor cell damage in a tumor treated with a chemotherapeutic agent. Supportive evidence was obtained using sublines of UMSCC10b selected for cDDP resistance. The parental cells, the 3-fold resistant subline UMSCC10b-Pt/S6 (15,16), and the 6-fold resistant subline UMSCC10b-Pt/S15 (15,16) were exposed to 2, 7, 12 μM cDDP for 1 h. These levels of exposure correspond to the $IC_{10}$, $IC_{50}$, and $IC_{70}$ for the parental cell line, respectively. FIG. 4a indicates that the magnitude of the increase in GADD153 mRNA level in the 3-fold resistant variant was lower than in the parental cells. In the 6-fold cDDP-resistant variant, the expression of GADD153 did not increase above its baseline level following exposure to these cDDP concentrations.

The UMSCC10b-Pt/S6 and LTMSCC10b-Pt/S15 sublines, that sustain less lethal injury than the parental cells at a given concentration of cDDP, had proportionately smaller increases in GADD153 message. When the cells lines were compared at concentrations of cDDP that produced the same clonogenic survival, the magnitude of increase in GADD153 mRNA was the same for all 3 lines.

TABLE 1

Identification of Sequences Having Sequence Identifiers

| SEQ. ID NO: | DESCRIPTION |
|---|---|
| 1 | GADD153, CAT ACA TCA CCA CAC (Sense) |
| 2 | GADD153, TGA CCA CTC TGT TTC (Anti-Sense) |
| 3 | β-ACTIN, GAG CGG GAA ATC GTG CGT GAC ATT (Sense) |
| 4 | β-ACTIN, GAT GGA GTT GAA GGT AGT TTC GTG (Anti-Sense) |

EXAMPLE 1

Prognostic Method for Tumor Clinical Response to Cisplatin

Figure 1:
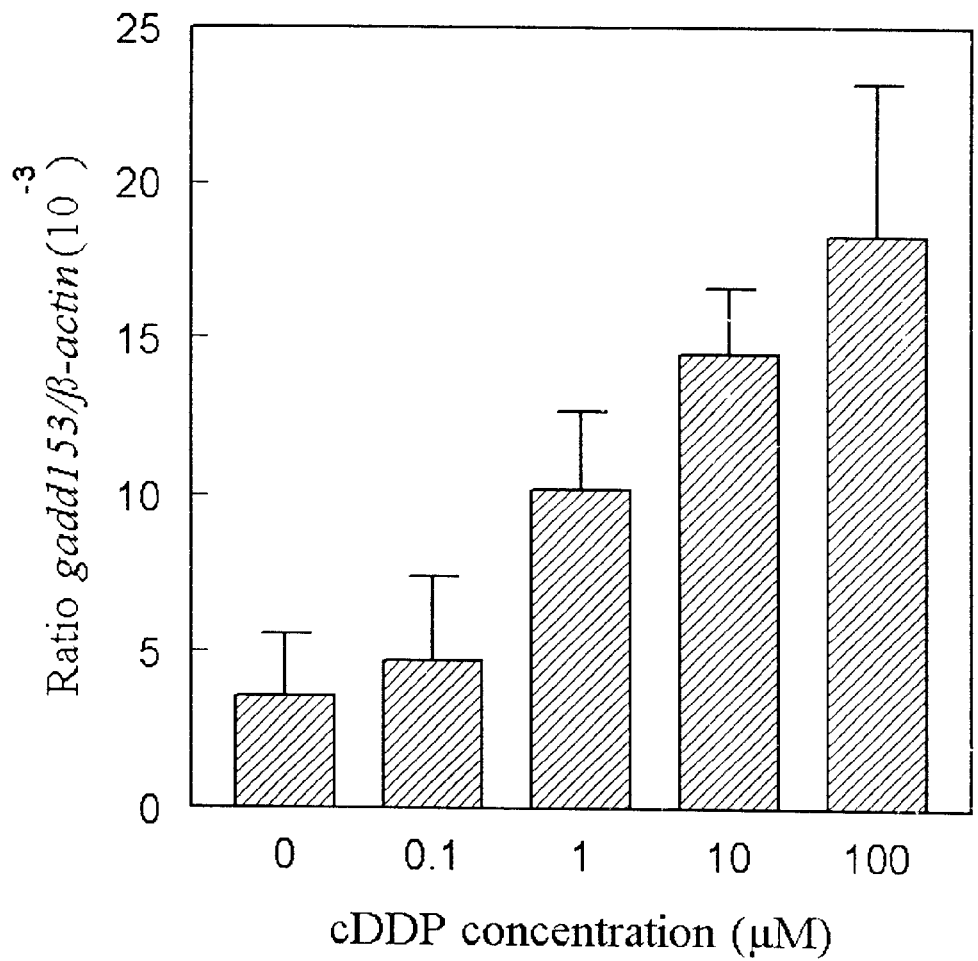
FIG. 1. The effect of cDDP on GADD153 mRNA levels in UMSCC10b cells. Exponentially growing cultures were treated with various cDDP concentrations for 1 h and then grown in drug-free medium for 24 h. The levels of GADD153 were quantified by RT-PCR. Error bars, ±SD.
Figure 2:
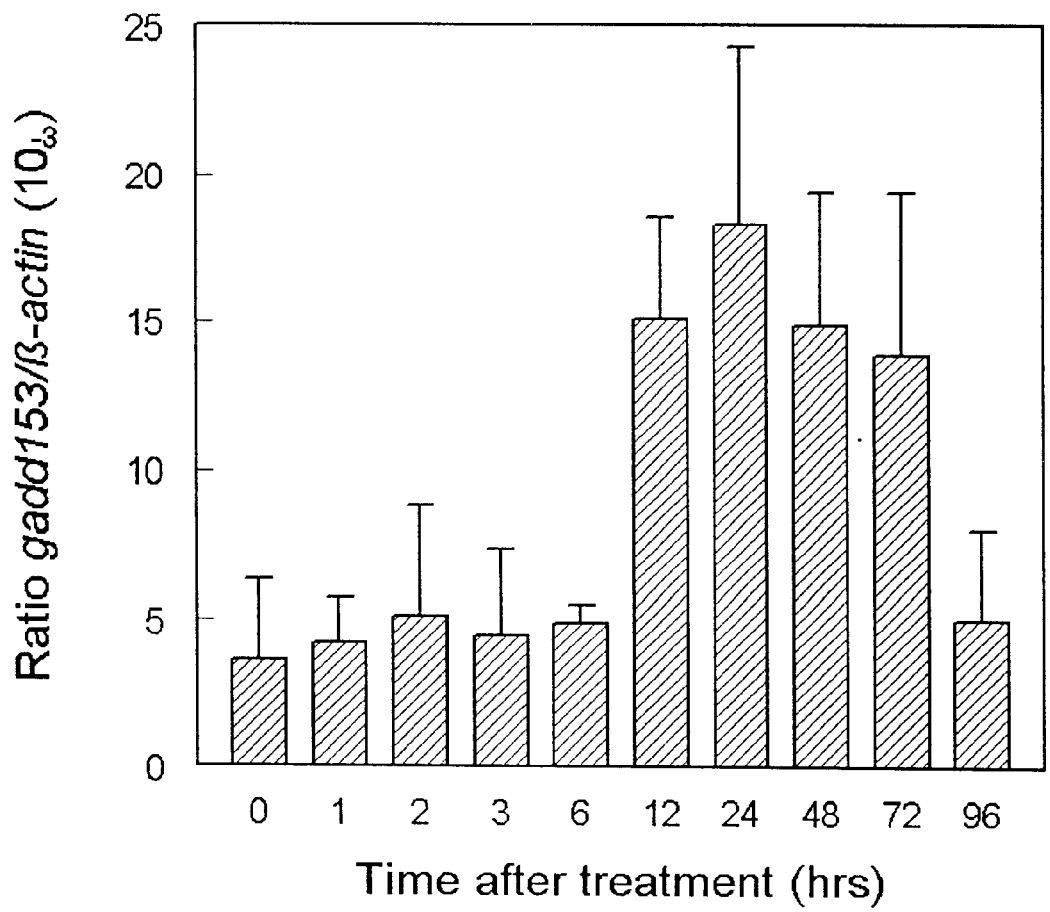
FIG. 2. Time course of cDDP-induced change in GADD153 mRNA level in LTMSCC10b cells in vitro. Cells were exposed to 100 $\mu$M cDDP for 1 h and incubated in drug-free medium for various periods of time prior to the harvesting of RNA. Error bars, ±SD.

In order to permit use of needle aspiration biopsies of tumors, the highly sensitive technique of RT-PCR rather than the less sensitive technique of Northern blot analysis was utilized throughout for quantitation of mRNA. The magnitude of the change in GADD153 mRNA level as a function of cisplatin (cDDP) concentration was determined by treating UMSCC10b cells with 0.1, 1, 10, or 100 μM cDDP for 1 h and quantifying GADD153 mRNA in untreated and treated cells harvested at 24 h by RT-PCR. The procedure is detailed in the attached examples. The results in FIG. 1 indicate that a concentration-dependent magnitude of increase in GADD153 mRNA levels reached 6-fold at the highest cDDP concentration tested. FIG. 2 depicts the time course of increase in GADD153 following a 1 h exposure to 100 μM cDDP. An increase in GADD153 mRNA level was evident at 12 h after cDDP exposure, and the peak occurred at 24 h followed by a decline to baseline levels by 96 h. β-ACTIN was used as an internal standard to normalize the data.

Figure 3:
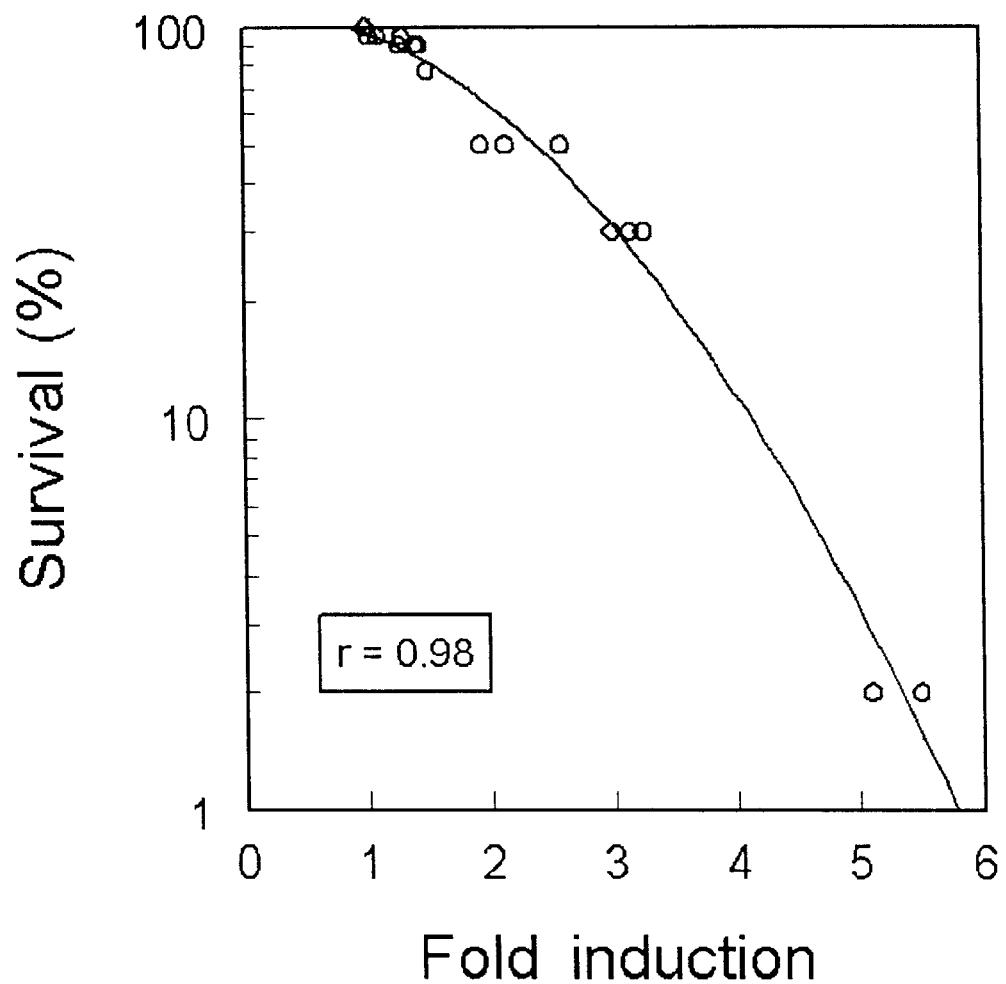
FIG. 3. Correlation between cell kill and the level of GADD153 expression in UMSCC10b cells in vitro. The r value of the best fitting curve was 0.98

The results in FIG. 3 indicate that the magnitude of the increase in GADD153 mRNA reflects the extent of tumor cell injury, since a good correlation between clonogenic survival and magnitude of increase in GADD153 mRNA level following treatment of UMSCC10b cells with increasing concentrations of cDDP was observed.

The magnitude of the change in GADD153 mRNA level in the xenografts increased with increasing cDDP dose over a range in which UMSCC10b tumors are known to be responsive. These results confirm that the increase in GADD153 depends on the extent of injury caused by the drug.

Figure 4B:
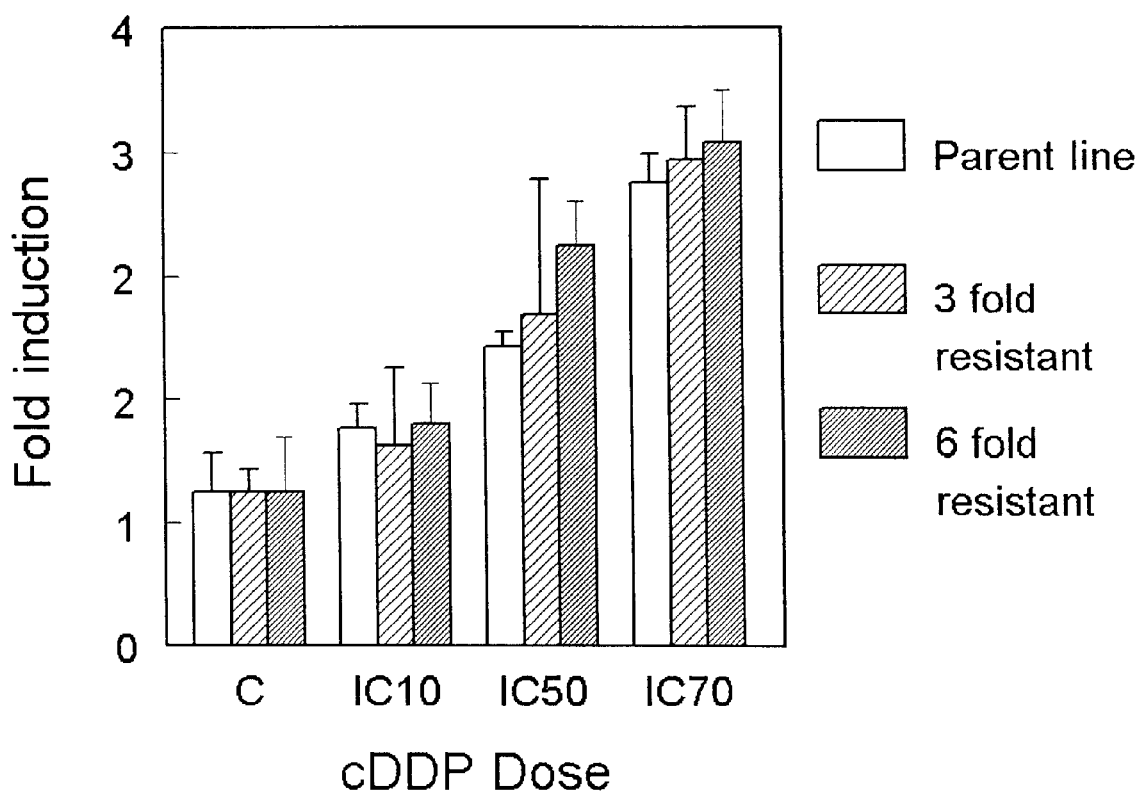

A cDDP concentration that was highly toxic to the sensitive parental cells and resulted in a high level of GADD153 expression failed to produce any increase in GADD153 message level in resistant cells in which there was little toxicity. To assure that the resistant variants had not lost their capacity to activate the GADD153 gene, and to validate the change in GADD153 level as a molecular marker of tumor injury in drug resistant as well as sensitive cells, the effect of cDDP applied at equitoxic concentrations was compared between the parental cells and the two resistant sublines. As shown in FIG. 4b, no difference between the cell lines in the change in expression of GADD153 was detected at the 3 different levels of cytotoxicity tested ($IC_{10}$, $IC_{50}$, $IC_{70}$), indicating that the extent of cellular injury is a determninant of the level of GADD153 mRNA expression.

Figure 5A:
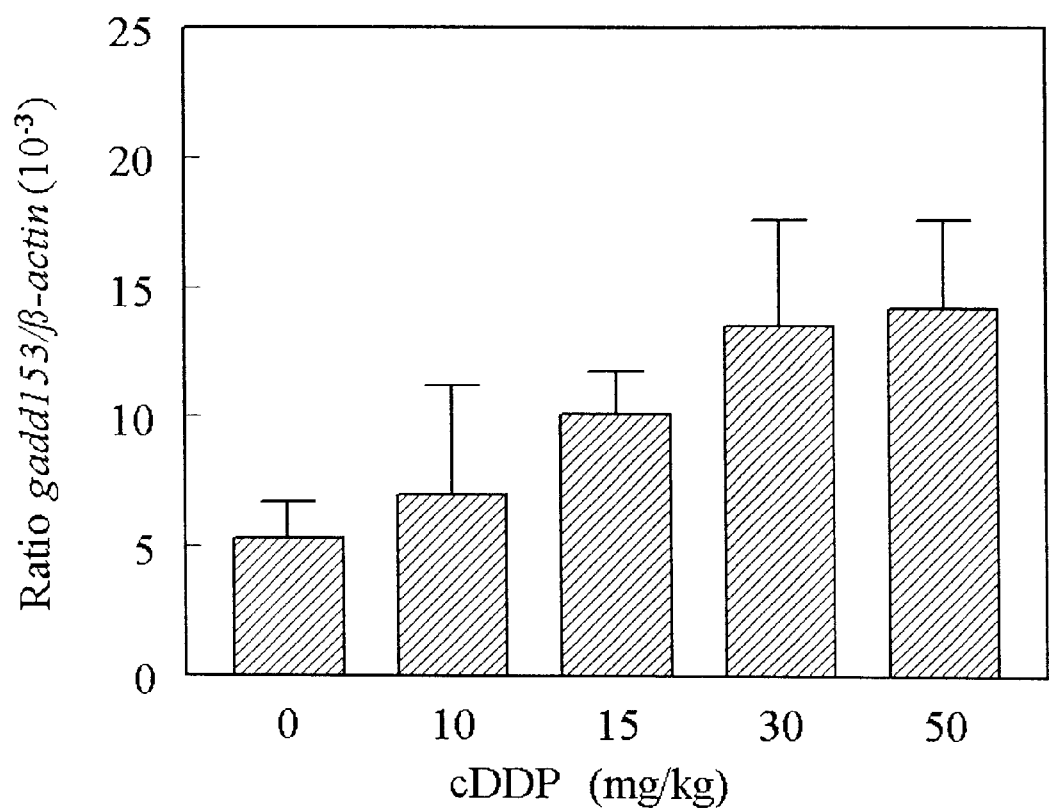
FIGS. 5a and 5b. Change in GADD153 mRNA levels in UMSCC10b xenografts growing in nude mice. The effect of cDDP dose on the level of GADD153 mRNA is demonstrated in FIG. 5a, and the effect of time post-treatment is demonstrated in FIG. 5b. Note that the scale of the ordinate differs for the two graphs.
Figure 5B:
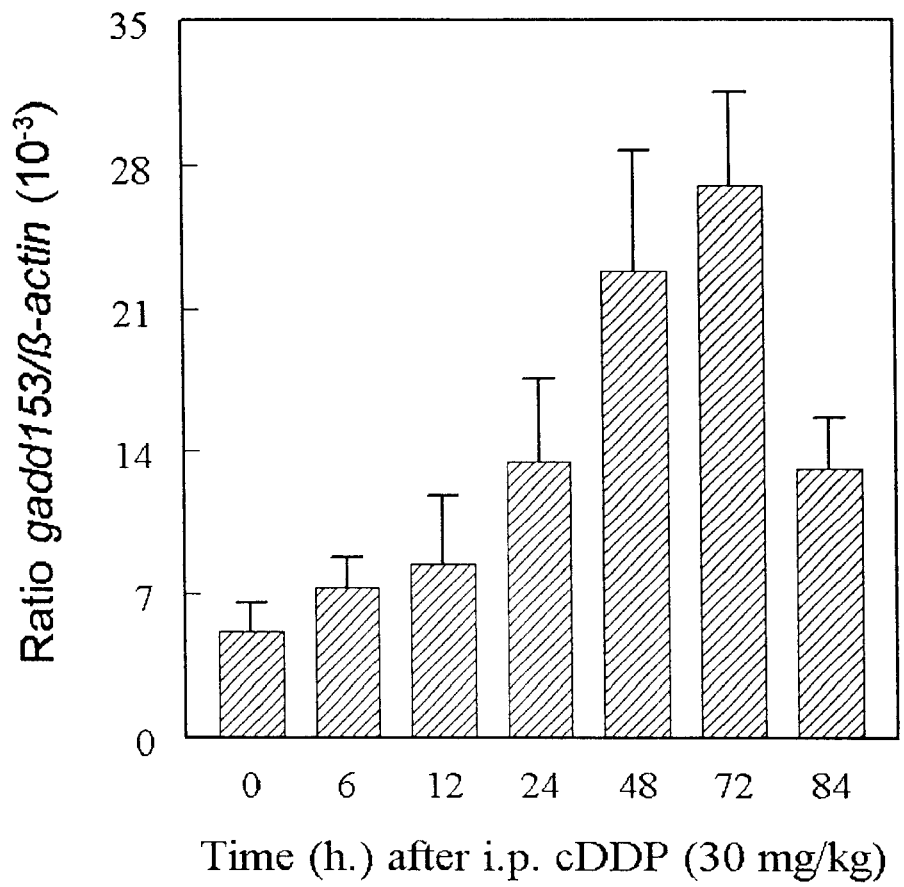

The various aspects of the invention are also useful for xenografted tumors. Nude mice were inoculated s.c. with human UMSCC10b tumor cells, and then treated with cDDP (0, 10, 15, 30 or 50 mg/kg cDDP i.p.) when the tumors reached 1 ml in volume. FIG. 5a depicts the results obtained when tumors were harvested at 24 h after cDDP treatment. As was the case for UMSCC10b cells exposed to cDDP in vitro, GADD153 mRNA levels increased as a function of cDDP dose. The time course of the change in message level in the xenografts was similar to that observed with in vitro exposure of the cells (FIG. 5b). Thus, GADD153 mRNA levels can be increased in vivo by cDDP doses around the maximum tolerated dose in this system (15–20 mg/kg cDDP). Although, the increase in GADD153 mRNA level was transient in vivo and returned to toward basal levels within about 96 hours after treatment, the data indicates that the magnitude of increase, above baseline, in GADD153 mRNA level can be used as a molecular marker of tumor cell injury in patients.

The methods of the invention employ a sample derived from a tumor. The sample can be obtained from a patient by way of surgical, needle or other biopsy. A needle biopsy samples only a limited portion of a tumor, and regional variation in histology, chemotherapeutic agent delivery and cellular response may be expected. Although it is contemplated that some variation may be obtained for the magnitude of increase in GADD153 mRNA according to where and how a biopsy is taken from a tumor, the present inventors have discovered that the induction of the GADD153 gene can be quantitated with a sufficiently small coefficient of variation. The magnitude of increase in GADD153 mRNA in 3 to 5 biopsies obtained from different portions of the same tumor mass in each of 4 cancer patients 24 h after administration of cytotoxic therapy was determined. The same was done with a UMSCC10b xenograft growing in nude mice after treatment with cDDP. The data (not shown) indicated that the coefficient of variation ranged between about 20 to about 29%, which demonstrates a relatively high reproducibility of the assay itself and a relatively small effect of potential regional heterogeneity within the tumor tissue. Thus, GADD153 mRNA levels can be quantitated with a sufficiently small coefficient of variation to make the present invention advantageous over known prognostic methods for tumor clinical response.

The sample derived from the tumor can be a resected tissue, homogenate, blend, extract, whole cell mixture, broken or disrupted cell mixture, a biological fluid, DNA, RNA, paraffin section and frozen tissue section.

Figure 6:
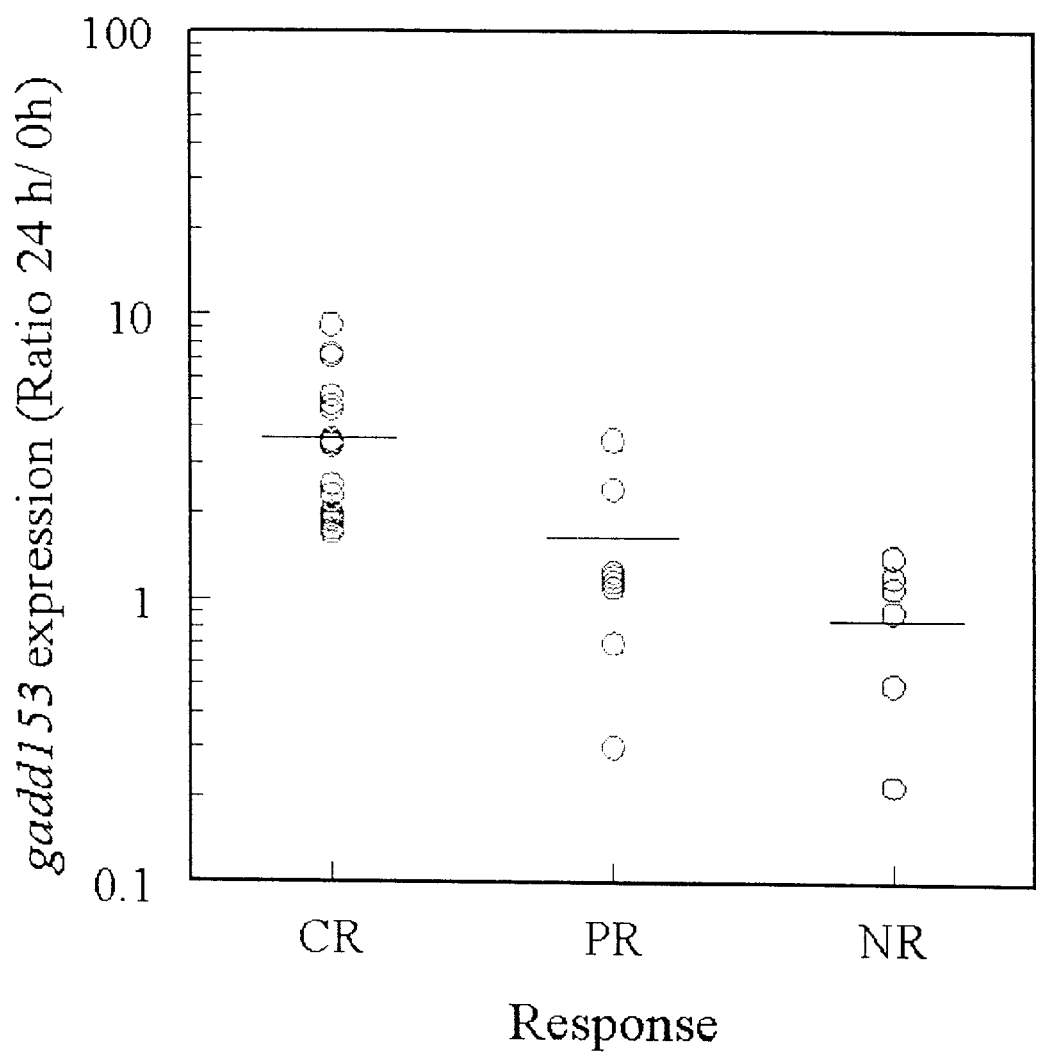
FIG. 6. Change in GADD153 mRNA levels in patients attaining either a complete (CR) or partial (PR) regression or tumor progression (NR) to cDDP-based treatment. The increase in GADD153 MRNA level was significantly higher in the CRs compared to either the PRs or NRs (p<0.05 and p<0.005, respectively, determined by one way ANOVA, Scheffe's Procedure).

The present inventors have also discovered that the prognostic method for clinical response by a tumor to a chemotherapeutic agent can accurately predict a corresponding therapeutic response by a patient even though there exist several sources for potential variation. The relationship between the change in GADD153 mRNA level at 24 h after the start of the first course of treatment with cDDP or cDDP plus radiation therapy and subsequent tumor clinical response to this therapy in 32 patients with stage IV head and neck cancer was examined. The data for each patient is summarized in FIG. 6.

In the first group (indicated by CR in FIG. 6), 17 of the 32 patients attained a complete regression of the tumor. In this group, the magnitude of increase, above baseline, in GADD153 mRNA ranged from 2 to 9-fold with a mean of 3.8±2.2 (SD)-fold.

In the second group (indicated by PR in FIG. 6), 8 of the 32 patients achieved a partial regression. Only 4 of these had a magnitude of increase, above baseline, in GADD153 mRNA that ranged from 1.3 to 3.5-fold. The mean for all 8 patients was 1.6±0.9 (SD)-fold.

The third group (indicated by NR in FIG. 6) included 7 patients who had tumor progression, i.e. favorable therapeutic response, and their mean magnitude of increase, above baseline, in GADD153 mRNA was 0.8±0.5 (SD)-fold. The magnitude of increase, above baseline, in GADD153 mRNA induction for the CRs was statistically significantly different from that observed for both the PRs ($p<0.05$) and NRs ($p<0.005$). The value for the partial responders (PRs) differed from that of the non-responders (NRs, $p<0.05$). A magnitude of increase in GADD153 mRNA of 1.75-fold or higher predicted a complete response with a sensitivity of 94% and a specificity of 87%. It should be noted that even though there was an overlap in the observed ranges for magnitude of increase in GADD153 mRNA, the present prognostic method accurately predicted the clinical response of a tumor in a patient to a chemotherapeutic agent.

Prognostic Method for Tumor Clinical Response to Paclitaxel

This embodiment of the invention provides a prognostic method for tumor clinical response in patients receiving paclitaxel alone or in combination with high dose progesterone (PROTAX). GADD153 is used as a molecular marker for the detection or prediction of tumor clinical response and patient therapeutic response.

Figure 7:
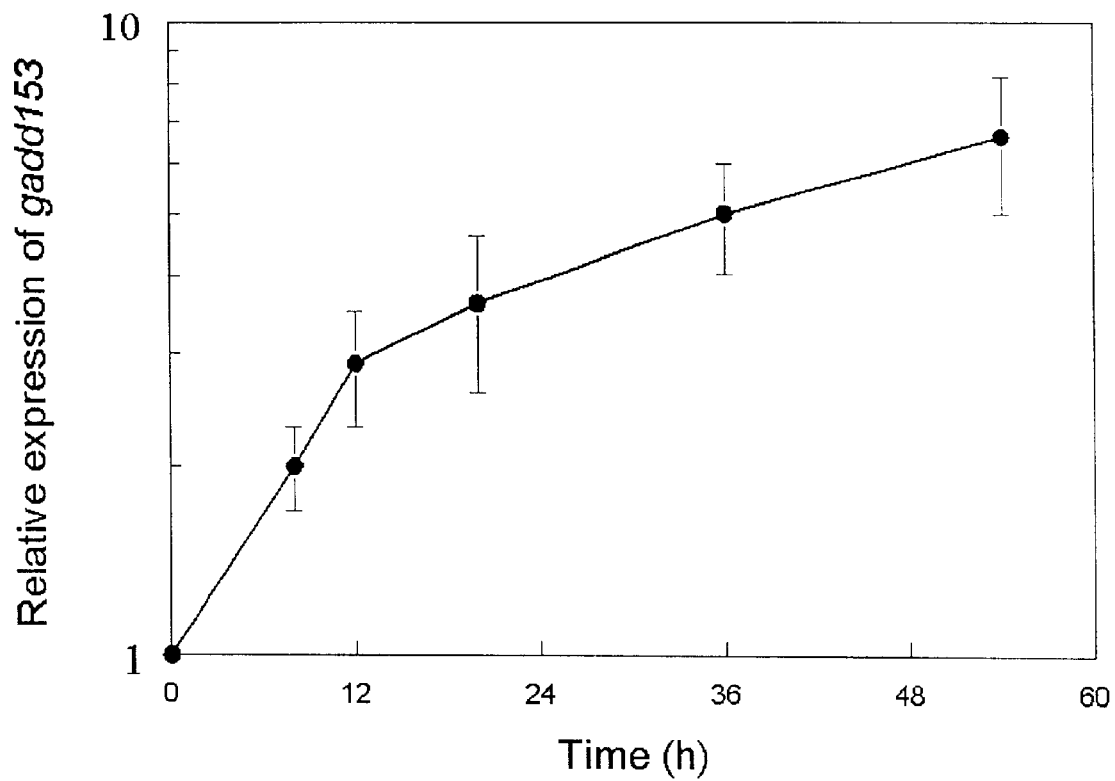
FIG. 7. Does response curve of 2008 ovarian cancer cells to one hour incubation with paclitaxel. Relative GADD153 expression quantitated by Northern Blot.

FIG. 7 shows the change in GADD153 mRNA level in 2008 ovarian carcinoma cells as a function of paclitaxel concentration. The cells were exposed to paclitaxel for 24 h over a concentration range corresponding to 1–10 times the $IC_{50}$ prior to extraction of RNA. These results demonstrate that RT-PCR detects a paclitaxel concentration-dependent increase in GADD153 mRNA which is consistent with previous results above. At a concentration 10 times the $IC_{50}$, there was a 5.7±2.5-fold increase in GADD153 mRNA level at 24 hours.

Figure 8A:
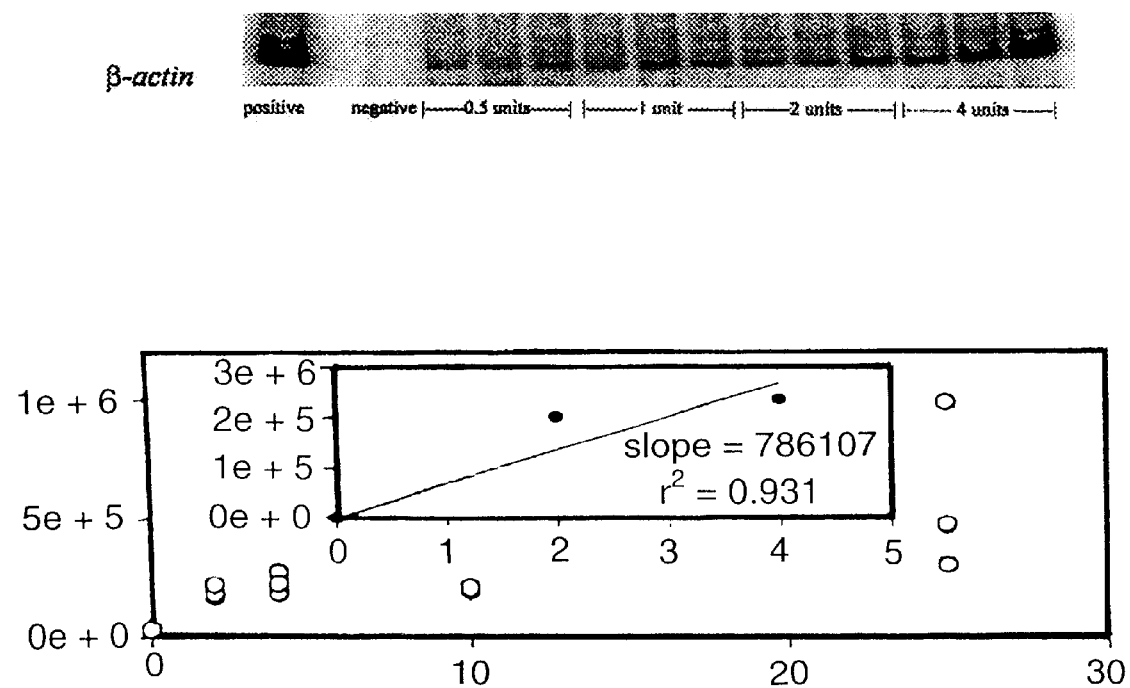
FIGS. 8a–8c Representative linear regression graphs of genes studied with their Molecular Imager images. X-axes are units of cDNA and y-axes are the measured amounts of $^{32}$p incorporation, in arbitrary units. Open and filled diamonds are individual band measurements and the means at a specific dilution, respectively.
Figure 8B:
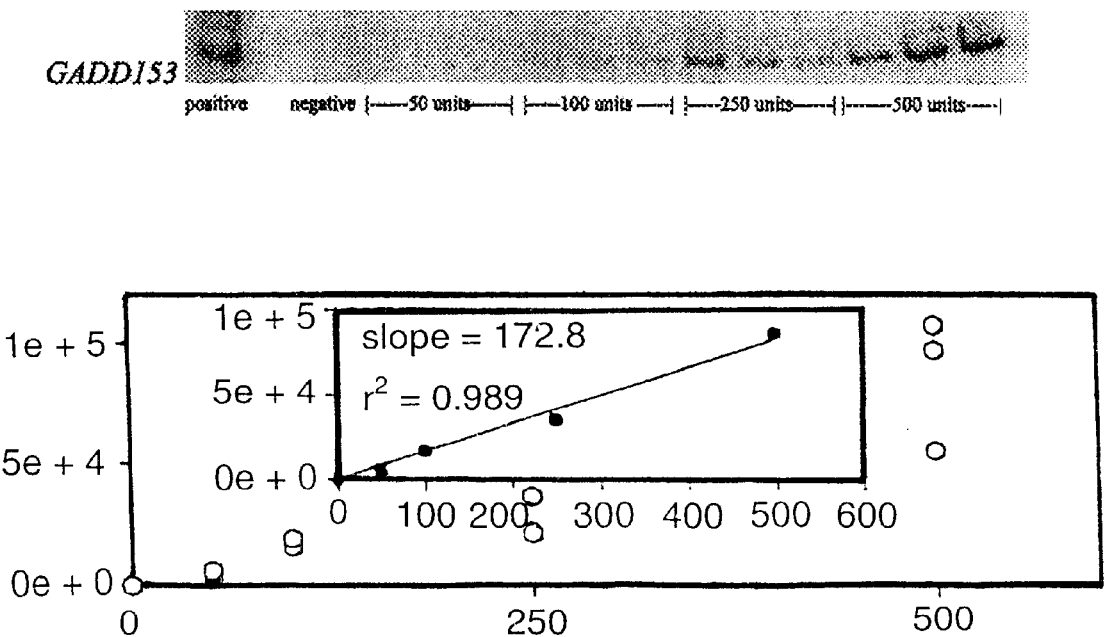
Figure 8C:
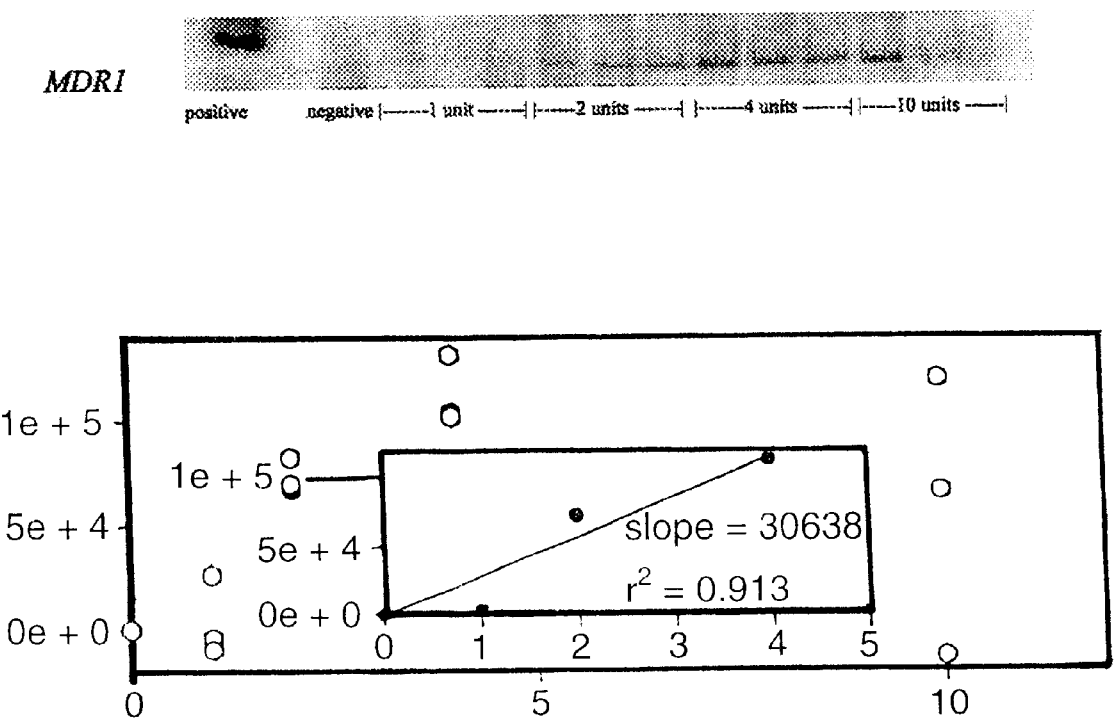

FIGS. 8a–8c show a representative analysis of β-ACTIN and GADD153. Each cDNA sample was examined to identify the range over which the amount of PCR product varied linearly with the extent of dilution of the original cDNA sample. The slope of the regression line for β-ACTIN was dependent on the amount of starting material obtained in the needle aspirations. The samples that showed minimal amounts of starting material, determined by ethidium bromide quantitation, also reflected smaller slopes after PCR amplification and linear regression analysis. This data was used to design the following study.

A group of 19 patients, which tumors and clinical responses to chemotherapy are listed in Table 2, had their tumors biopsied by fine needle aspiration before and 24 h after each cycle of PROTAX administered. Of the nineteen patients, the samples from 14 of these were analyzable by RT-PCR for the basal and induced expression of GADD153. The relative levels of GADD153 gene expression was determined by comparing the ratio of RT-PCR products derived from the GADD153 gene and an endogenous internal standard gene, in this case β-ACTIN(2,12,20).

As shown in Table 3, there was a difference with respect to the treatment-induced change in GADD153 mRNA level among the 14 patients in this study from whom adequate mRNA was available. Seven patients had no response, on the cycle of therapy analyzed, to treatment with PROTAX, and 7 patients had either a minimal or partial response. There was no difference in basal GADD153 mRNA level between responders and non-responders; however, there was a significantly greater increase in GADD153 mRNA at 24 in responders than non-responders ($p=0.005$).

TABLE 2

Patient Characteristics

| Patient # | Cycle | Patient Response*** | Primary tumor |
|---|---|---|---|
| 1 | 1 | PD | Ovarian Adenocarcnoma |
| 2 | 3 | PD | Endometrial Adenocarcinoma |
| 3 | 1 | PD | Squamous Cell Cancer of the Throat |
| 4 | 1 | PD | Squamous Cell Cancer of the Lung |
| 5 | 9 | MR | Ovarian Adenocarcinoma |
| 5 | 1 | PR | Ovarian Adenocarcinoma |
| 6 | 1 | PD | Squamous Cell Cancer of the Mandible |
| 7 | 1 | MR | Squamous Cell Cancer of the Tongue |
| 8 | 1 | PD | Ovarian Adenocarcinoma |
| 9 | 1 | PD | Breast Cancer |
| 10 | 1 | MR | Ovarian Adenocarcinoma |
| 11 | 1 | PR | Large Cell Lymphoma |
| 12 | 1 | PR | Colon Cancer |
| 13 | 1 | PD | Breast Cancer |
| 14 | 5 | MR | Colorectal Cancer |
| 15 | 1 | PD | Nasopharyngeal Cancer |

***
PD = Progressive Disease
MR = Minimal Response (25–50% reduction in tumor size)
PR = Partial Response (>50% reduction in tumor size)

TABLE 3

GADD153 mRNA Levels in Tumor Biopsies

| | | GADD153 mRNA Level | |
|---|---|---|---|
| Patient | Response | Before Treatment | 24 h. after Treatment |
| a | PD | 0.078 | 0.0001 |
| b | PD | 0.057 | 0.002 |
| c | PD | 0.126 | 0.003 |
| d | PD | 0.007 | 0.007 |
| e | PD | 0.667 | 0.135 |
| f | PD | 0.021 | 0.016 |
| g | PD | 1.279 | 0.152 |
| f | MR | 0.197 | 0.275 |
| h | PR | 0.005 | 0.112 |
| I | PR | 0.109 | 0.002 |
| j | MR | 0.129 | 0.191 |
| k | MR | 0.022 | 0.083 |
| l | PR | 0.117 | 0.493 |
| m | PR | 0.063 | 0.5208 |

PD = Progressive Disease
MR = Minimal Response
PR = Partial Response

All patients with tumor progression (n=7) had no increase in GADD153 mRNA at 24 h when compared with the sample obtained immediately before paclitaxel infusion (mean SD increase 0.3±0.4-fold). However, 4 of 7 patients with "minimal" response (<50 but >25% reduction in volume) and 3 of 7 with "partial" response (>50% reduction in the volume of measurable disease 50%) had an increase in GADD153 mRNA level indicative of tumor damage or cell kill. Six of 7 patients with either a minimal response or a partial response had an increase in GADD153 mRNA level 24 hours after treatment (p=0.005, Fisher's exact test). The increase in GADD153 mRNA level ranged from 1.4 to 8.24-fold with a mean of 3.0 ±2.7-fold (SD). A magnitude of increase, above baseline, in GADD153 mRNA level of 1.5-fold or higher predicted response with a sensitivity of 86% and a specificity of 100%. Thus, in this particular embodiment, the present invention provides a prognostic method for the clinical response of tumors to chemotherapy which is predictive of responders, those with minimal, partial or full tumor regression, and non-responders, those with tumor progression.

One way analysis of variance (Scheffe's procedure) was used to evaluate the significance of differences in the magnitude of the change in GADD153 level between patients who achieved either a complete or partial regression or disease progression. In some embodiments, Fisher's exact test was used to evaluate contingency tables.

DNAse was obtained from Epicentre Technologies; DTT, 5× MMLV and MMLV Reverse Transcriptase were obtained from Gibco/BRL; BSA, dNTP's, random hexamers ($rdN_6$) and RNAguard (RNAse inhibitor) were obtained from Pharmacia; 10× Taq Buffer, 25 mM $MgCl_2$ and Ampli-Taq were obtained from Applied Biosystems; $^{32}$P-dCTP was obtained from ICN Radiochemicals. All chemicals and buffers were molecular biology grade.

The chemotherapeutic agents contemplated by the invention may be of synthetic or natural origin. Such agents include, by way of example and without limitation, antineoplastics, cytotoxic agents, adriamycin, fluorouracil, methotrexate, asparaginase, cytostatic agents, alkylating agents; Alkyl Sulfonates such as Busulfan, Improsulfan, Piposulfan; Aziridines such as Benzodopa, Carboquone, Meturedopa, Uredopa; Ethylenimines and Methylmelamines such as Altretamine, Triethylenemelamine, Triethylenephosphoramide, Triethylenethiophosphoramide, Trimethylolomelamine; Nitrogen Mustards such as Chlorambucil, Chlornaphazine, Cholophosphamide, Estramustine, Ifosfamide, Mechlorethamine, Mechlorethamine Oxide Hydrochloride, Melphalan, Novembichin, Phenesterine, prednimustine, Trofosfamide, Uracil Mustard; Nitrosoureas such as Carmustine, Chlorozotocin, Fotemustine, Lomustine, Nimustine, Ranimustine; Antibiotics such as Aclacinomycins, Actinomycin $F_1$, Actinomycin D, Authramycin, Azaserine, Bleomycins, Cactinomycin, Carubicin, Carzinophilin, Chromomycins, Dactinomycin, Daunorubicin, 6-Diazo-5-oxo-L-norleucine, Doxorubicin, Epirubicin, Mitomycins, Mycophenolic Acid, Nogalamycin, Olivomycins, Peplomycin, potfiromycin, Puromycin, Streptonigrin, Streptozocin, Tubercidin, Ubenimex, Zinostatin, Zorubicin; Antimetabolites; Folic Acid Analogs such as Denopterin, Methotrexate, Pteropterin, Trimetrexate; Purine Analogs such as Fludarabine, such as Denopterin, Methotrexate, Pteropterin, Trimetrexate; Purine Analogs such as Fludarabine, 6-Mercaptopurine, Thiamiprine, Thioguanaine; Pyrimidine Analogs such as Ancitabine, Azacitidine, 6-Azauridine, Carmofur, Cytarabine, Dideoxyuridines, Doxifluridine, Enocitabine, Floxuridine, Fluororacil, Tegafur; Aceglatone, others such as Aldophosphamide Glycoside, Aminolevulinic Acid, Amsacrine, Bestrabucil, Bisantrene, Carboplatin, Cisplatin, Defofamide, Demecolcine, Diaziquone, Elliptinium Acetate, Etoglucid, Etoposide, Gallium Nitrate, Hydroxyurea, Interferon-α, Interferon-β, Interferon-γ, Interleukine-2, Lentinan, Lonidamine, Mitoguazone, Mitoxantrone, Mopidamol, Nitracrine, Pentostatin, Phenamet, Pirarubicin, podophyllinice Acid, 2-Ethylhydrazide, Procarbazine, PSK®, Razoxane, Sizofiran, Spirogermanium, Tamoxifen, Taxol, Teniposide, Tenuazonic Acid, Triaziquone, 2,2',2"-Trichlorotriethylamine, Urethan, Vinblastine, Vincristine, Vindesine, Dacarbazine, Mannomustine, Mitobronitol, Mitolactol, Tamoxifen and Pipobroman; Androgens such as Calusterone, Dromostanolone Propionate, Epitiostanol, Mepitiostane, Testolactone; Antiadrenals such as Aminoglutethimide, Mitotane, Trilostane; Antiandrogens such as Flutamide, Nilutamide; Antiestrogens such as Aromatase Inhibiting 4(5)-Imidazoles; Folic Acid Replenisher such as Frolinic Acid; steroids, paclitaxel, progesterone in combination with paclitaxel, etoposide, topoisomerase inhibitors, DNA interealators, cycloheximide, daunorubicin, camptothecin and natural murine products.

EXAMPLE 2

Cell Lines of Human Head and Neck Squamous Cell Carcinoma

The UTMSCC10b cell line was derived from a human head and neck squamous cell carcinoma (14). Cells were cultured at 37° C. under 5% $CO_2$ in 150 cm² flasks (Corning, Corning, N.Y.) with RPMI 1640 medium (Mediatech Inc., Hemdon, Va.) containing 10% fetal bovine serum (Gemini Bioproducts Inc., Calabasas, Calif.), 2 mM L-glutamine and 100 units/ml of penicillin G and 100 μg/ml of streptomycin sulfate. Cells were subcultured after reaching confluence (approximately $5 \times 10^7/150$ cm²) by trypsinization and replating at a density of approximately $10^7$ cells/150 cm².

EXAMPLE 3

Selection for cDDP Resistance

UMSCC10b cells were selected for cDDP resistance by chronic exposure to cDDP which was supplied by (Bristol-Meyers-Squibb, Princeton, N.Y.). The first three selections were performed at a concentration of 0.5 μM which allowed approximately $10^7$ cells to grow to confluence in a 150 cm² flask within one week. For every following set of 3 selections, the cDDP concentration was increased by approximately 20% (15,16).

EXAMPLE 4

Tumor Biopsy: General Method

Tumor tissue specimens were obtained by fine needle aspiration immediately before treatment and at 24 hours after the start of drug infusion. Part of the biopsy was used for cytology to determine the percentage of tumor cells. The rest of the biopsy was added to Buffer D [4 M guanidine isothiocyanate, 25 mM sodium citrate, pH 7, 0.5% Sarcosyl and 0.1 M 2-mercaptoethanol], homogenized and prepared for RNA extraction.

EXAMPLE 5

Sensitivity to cDDP in vitro

The sensitivity of the UMSCC10b cell line and its cDDP-resistant variants to cDDP was determined by clonogenic assay using a 1 h cDDP exposure. A single-cell suspension was plated into 60 mm tissue culture dishes (Corning) at 300 cells per dish in fresh medium. After incubation for 24 h at 37° C., cells had attached to the plates and cDDP was added to the cells and incubated for 1 h following which the cells were washed twice with phosphate-buffered saline and 5 ml of fresh medium was added. Cultures were incubated for an additional 13–15 days following which there were fixed with methanol, stained with Giemsa, and clusters of >50 cells were scored as colonies. cDDP-selected cells were cultured in drug-free media for 2 weeks before cDDP sensitivity was determined by clonogenic assay.

EXAMPLE 6

Tumor Xenografts in Mice

UMSCC10b cells were injected subcutaneously over the shoulder of athymic (BALB/c nu/nu) female mice, 3–4 weeks of age (Harlan Sprague Dawley, Indianapolis, Ind.). The xenografts were allowed to grow until they reached approximately 1 mm³ in volume, at which time cDDP treatment was initiated.

EXAMPLE 7

Expression of GADD153 in vitro

To determine the time course of the change in GADD153 mRNA level, UMSCC10b cells were incubated with 100 μM cDDP for 1 h and total RNA was extracted at 0, 1, 2, 6, 12, 24, 48, 72 and 96 h after treatment. To analyze the effect of cDDP concentration on the expression of GADD153, UMSCC10b cells were incubated for 1 h with various cDDP concentrations (0, 0.1, 1, 10, 100 and 1000 μM) and RNA was extracted 24 h after cDDP exposure.

EXAMPLE 8

Expression of GADD153 in vivo

One set of nude mice bearing UMSCC10b xenografts were injected i.p. with a single dose of cDDP (15, 30, 50, or 100 mg/kg), and total RNA was isolated from the xenograft excised 24 h later. To analyze the time course of the change in GADD153 mRNA level, mice bearing UMSCC10b xenografts were treated with a single injection of cDDP (30 mg/kg) and sacrificed at 0, 24, 48, 72, and 96 h after treatment. In both sets of studies, the excised tumors were minced in guanidine isothiocyanate with a polytron (Biospec Products Inc., Bartlesville, Okla.), and stored at 4° C. until all tumors were processed. The RNA was transcribed to cDNA using random beamer primers.

EXAMPLE 9

Patient Selection and Treatment

Thirty-two patients with previously untreated stage IV head and neck cancer were treated at the UCSD Cancer Center on a phase I/II experimental protocol. All patients had been considered to have unresectable tumors. All patients received i.a. cDDP (150–200 mg/M²) and i.v. sodium thiosulfate infusion concurrently. The details of this treatment program have been published elsewhere by the present inventors (17,18), which description is specifically incorporated herein by reference. cDDP was dissolved in 400 ml of 0.9% saline and infused over 3–5 minutes through a microcatheter placed angiographically to selectively encompass the dominant blood supply of the targeted tumor. Simultaneous with the cDDP infusion, sodium thiosulfate was infused i.v. at a dose of 9 g/m² dissolved in 300 ml of distilled water over 3 minutes, followed by 12 g/m² dissolved in one liter of distilled water over 6 h by continuous infusion to prevent severe nephrotoxicity. Treatment was repeated weekly for a total of 4 doses. In addition, 17 of the 32 patients received radiotherapy in doses of 2 cGy/day (×35 fractions) starting concurrently with the start of cDDP treatment. Needle aspiration or small cutting needle biopsies were obtained just before and at 24 h following the first dose of cDDP. Tumor response was assessed at 2 months using criteria based on physical examination, repeat computed tomography/magnetic resonance imaging studies, and repeat endoscopy and biopsy.

EXAMPLE 10

Patient Selection and Treatment: Alternate Method

Nineteen patients were entered on this study, all of whom gave written informed consent before study entry in accordance with Federal, State and local guidelines. Sufficient mRNA was obtained from 14 patients for analysis of the change in GADD153 mRNA level. Table 1 provides information on the characteristics of the patients entered on this study. All patients had measurable disease, and all had been heavily pretreated with other chemotherapy regimens. Responses were defined as either partial (>50% reduction in tumor volume) or minimal (>25% but <50 reduction in tumor volume). No patient attained a complete response. Progesterone was first dissolved in ethanol at a concentration of 66.67 mg/ml and stored in 50 ml glass vials. On and administered as a 24 hour continuous infusion concurrently with 125 mg/$M^2$ paclitaxel (Taxol®, Bristol Meyers).

EXAMPLE 11

RNA Extraction

RNA was extracted from UMSCC10b cells using the acid guanidium thiocyanatephenol-chloroform extraction (19), and from UMSCC10b xenografts and human tumor biopsies in cesium chloride as follows.

UMSCC10b cells were harvested in 10 ml of denaturing solution (4 M guanidinium thiocyanate, 25 mM sodium citrate, pH 7, 0.5% sarcosyl, and 0.1 M 2-mercaptoethanol. After adding 1 ml of 2 M sodium acetate (pH 4), 10 ml of water-saturated phenol (pH 4) and 2 ml of chloroform:isoamyl alcohol (49:1) to the denatured cells, they were mixed thoroughly, placed on ice for 15 min, and centrifuged at 2800 rpm for 20 min at 4° C. The aqueous phase was collected and mixed with 10 ml of isopropyl alcohol, placed for 1 h at −20° C. and centrifuged. The pellet was dissolved in 1.8 ml of denaturing solution and 2 ml of isopropyl alcohol, placed for 1 h at −20° C. and centrifuged. The pellet was washed with 1 ml of 80% ethanol and then centrifuged at 5000 rpm for 10 min at room temperature. The RNA pellet was dried for 20 min in a tissue culture hood and resuspended in 100 μl of DEPC-treated water. Of this solution, 50 μl was used immediately for cDNA synthesis.

Tumor tissues obtained from either xenografts or tumor biopsies were minced in guanidine isothiocyanate (8ml) with a polytron (Biospec Products Inc., Bartlesville, Okla.), added to polyallomer ultracentrifuge tubes containing 4 ml of a 5 M cesium chloride solution, placed in a SW40Ti rotor and centrifuged at 32,000 rpm for 16 h at 20° C. The pellet was resuspended in 300 μl sodium acetate (pH 7), and 600 μl 100% ethanol was added. The RNA precipitated overnight at −70° C. and was resuspended in 50 μl DEPC-water.

EXAMPLE 12

RNA Extraction: Alternate Method

The procedure followed for RNA extraction was similar to that described by Sambrook et al. (21). Briefly, cells were lysed in Buffer D and the mixture was transferred to a 15 ml conical tube. Two molar sodium acetate, pH4 and water saturated phenol, pH 4 with chloroform/isoamyl alcohol (49:1), in this order, were then added to the tube. The tube was then shaken vigorously and incubated on ice for 15 minutes after which it was centrifuged for 15 minutes at 3000 rpm (2000×g) at 4° C. The aqueous phase was transferred to a new 15 ml tube. Next, one volume of 100% isopropanol was added, the tube was left at −20° C. for at least 1 hour and then centrifuged for 15 minutes at 3000 rpm, and the pellet was resuspended in Buffer D. Isopropanol was added to precipitate the RNA at −20° C. for at least 1 hour. The tube was centrifuged at 3000 rpm for 15 minutes to obtain an RNA pellet. The pellet was washed with cold 80% ethanol, transferred to a 1.5 ml tube and centrifuged for 15 minutes at 6000 rpm. The pellet was then dried by pipetting off excess ethanol and letting the tube air dry for 20 minutes. The RNA pellet was finally dissolved in DEPC-treated water and stored in −70° C. until cDNA synthesis.

EXAMPLE 13

PCR Quantitation of Extracted mRNA

GADD153 message levels were quantified using a modification of the technique reported by Horikoshi et al (20). Total RNA acquired from the biopsies or xenografts was reverse-transcribed using random hexamers to produce cDNA (20,21,22). Serial dilutions of the CDNA were made and 5 μl of each dilution was placed in a sterile 0.5 ml Eppendorf tube. Taq-mix (10 μl) containing 2.5 μl of 10×Taq buffer (100 mM of Tris hydrochloride, pH 8.3, 500 mm potassium chloride, Perkin-Elmer Cetus, Norwalk, Conn.), 0.5 μl of 10 mM dNTPs, 1.52 or 2.0 μl of a 25 mM magnesium chloride buffer, and 5.48 μl or 4.88 μl of sterile PCR water, respectively, were added. In addition, 10 μl primer mix was added containing: 1 μl of each of the sense and antisense primers (12.5 μM), 6 μl sterile PCR water, 1.87 μl total volume of l×Taq buffer and $^{32}$P-labeled DCTP (ratio 1×buffer: $^{32}$P-DCTP, 15:1) and 0.126 μl of Ampli-Taq DNA polymerase enzyme. Mineral oil was added to each tube. The tubes were placed in the thermocycler and amplified. Each set of PCR reactions contained at least one positive and one negative control (CDNA was substituted by sterile water). Each PCR reaction was performed in triplicate or quadruplicate. PCR products were separated on a 8 M (6%) acrylamide gel and analyzed using a Molecular Imaging System (BioRad, Hercules, Calif.). For each RNA sample to be analyzed, a series of PCR reactions was performed to generate a graph of the amount of PCR product as a function of input CDNA for both GADD153 and β-ACTIN. These data were fit to a regression line, and the result was expressed as the ratio of the slope of the regression line for GADD153 to that β-ACTIN. The primers listed below were synthesized by the Molecular Core Facility of the UCSD Cancer Center:

GADD153:CAT ACA TCA CCA CAC (sense) (SEQ ID No. 1)
   TGA CCA CTC TGT TTC (anti-sense) (SEQ ID No. 2)

β-ACTIN: GAG CGG GAA ATC GTG CGT GAC ATT (sense) (SEQ ID No. 3)
   GAT GGA GTT GAA GGT AGT TTC GTG (anti-sense) (SEQ ID No. 4)

EXAMPLE 14

PCR Quantitation of Extracted mRNA: Alternate Method

A modification of the method of Horikoshi et al. (20) was used for PCR. A stock solution was prepared by adding 20 μl of the cDNA sample isolated from the previous procedure to 80~1 sterilized water in 0.5 μl tubes, and dilutions ranging from 1:2 to 1:2,500 were made from this stock solution. To new sterile 0.5 ml centrifuge tubes were added 1.52 mM Taq Mix for β-ACTIN (10X Taq II Buffer, without $MgCl_2$; 25 mM $MgCl_2$; sterile water; 10 mM dNTP's; 0.5 M Spermidine) or 2 mM Taq Mix for GADD153 [same as Taq buffer for β-ACTIN but using different amounts of 25 mM MgCl$_2$ and sterile water] and their respective 3' and 5' primers. The primers used are listed below and were synthesized by the Molecular Core Facility of the UCSD Cancer Center.

GADD153: CAT ACA TCA CCA CAC (sense) (SEQ ID No 1)
TGA CCA CTC TGT TTC (antisense) (SEQ ID No. 2)

β-ACTIN: GAG CGG GAA ATC GTG CGT GAC ATT (sense) (SEQ ID No. 3)
GAT GGA GTT GAA GGT AGT TTC GTG (antisense) (SEQ ID No. 4)

Four cDNA dilutions were chosen based on the ethidium bromide quantitation and triplicate aliquots of each were added to the tubes. The dilutions for GADD153 were always lower than those for β-ACTIN because the expression of GADD153 averaged approximately 1000-fold and 20-fold less than that of β-ACTIN, respectively (33,34). A "hot start" was done to denature the cDNAs; sterile water, 1X Taq Buffer, Ampli-Taq polymerase and 1.26 mCi $^{32}$p-dCTP were then added to each tube. The PCR cycles were 2 minutes at 94° C. before the first cycle, then 1 minute at 94° C., 1 minute at 57° C. and 2 minute at 72° C. for 45 cycles. The PCR products were then stored at 4° C.

EXAMPLE 15 cDNA Synthesis

The RNA samples were transferred to sterile 0.5 ml tubes along with DNAse I at 37° C. for 30 minutes. The DNAse was later denatured by heating the tubes to 70° C. for 10 minutes. MMLV-RTase mix [RNAguard, 0.1 M DTT, 5X MMLV Buffer, 10 mM dNTP's, BSA, random primers] was added to the samples, followed by MMLV-RTase enzyme (2000U/ml). The reaction was incubated for 10 minutes at room temperature (25° C.), then for 45 minutes at 42° C. and finally for 3 minutes at 90° C. Another aliquot of MMLV-RTase mix was added and the reaction was incubated for 45 minutes at 42° C. and 10 minutes at 90° C. (Perkin-Elmer Thermocycler). RNAse A (2.5 mg/ml) was added and incubated at 37° C. for 30 minutes, to remove remaining RNA from the hybrid. The samples were then stored in 0.5 ml microfuge tubes at 20° C.

EXAMPLE 16

Measurement of cDNA Concentration by Ethidium Bromide Analysis

The Saran Wrap method was used to measure the amount of cDNA made from tumor mRNA (21). This semi-quantitative data was also used to determine what range of 4 dilutions to use in the PCR reaction (vide infra). If cDNA concentrations were barely detectable by this method, an additional PCR amplification of βACTIN was performed to determine whether enough cDNA was present to quantitate gene expression in these samples. Sufficient cDNA was present to quantitate change in GADD153 expression in 14 patients.

EXAMPLE 17

Quantitation of PCR Product

Polyacrylamide gel loading dye (5 μl) was added to each tube of PCR product from the previous procedure and these mixtures were electrophoresed on an 8% polyacrylamide gel. The bands of interest were quantified on a Biorad Molecular Imager using the Biorad Molecular Analyst software. The amount of PCR product is a function of input cDNA. The amounts of product from the four serial dilutions were used to fit regression lines for GADD153 and β-ACTIN and the results were expressed as the ratio of the slope of the regression line for GADD153 to that for β-ACTIN.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Bijscher M, Ralimsdorf H J, Liftin M, Karin M, Herrlich P. The activation of the c-fos gene by UV and phorbol ester: different signal transduction pathways converge to the same enhancer element. *Oncogene* 3: 301–311, 1988.

2. Futscher B W, Erickson L C. Changes in c-myc and c-fos expression in a human tumor cell line following exposure to bifunctional alkylating agents. *Cancer Res.* 50:62–66, 1990.

3. Rubin E, Kharbanda S, Gunji H, Weichselbaum R, Kufe D. cis-diamminedichloroplatinum (II) induces c-jun expression in human myeloid leukemia cells: potential involvement of a protein kinase C-dependant signaling pathway. *Cancer Res.* 52: 878–882, 1992.

4. Karin, M., Herrlich, P. Cis- and trans-acting genetic elements responsible for induction of specific genes by tumor promotors, serum factors, and stress. In: N. H. Colburn (ed.), Genes and signal transduction in multistage carcinogenesis, pp.425–440. New York: Marcel Dekker, Inc., 1989.

5. Holbrook, N. J., Fornace, A. J. Response to adversity: molecular control of gene activation following genotoxic stress. *New Biol.* 3: 825–833, 1991.

6. Luethy, J. D., Fragnoli, J., Park, J. S., Fornace Jr, A. J., Holbrook, N. J. Isolation and characterization of the hamster GADD153 gene. *J. Biol. Chem.* 265: 16521–16526, 1990.

7. Park, J. S., Luethy, J. D., Wang, M. G., Fargnoli, J., Fornace, A. J., Jr; McBride, O. W., Holbrook N. J. Isolation, characterization and chromosomal localization of the human GADD153 gene. *Gene,* 116: 259–267, 1992.

8. Fornace Jr, A. J., Nebert D. W., Hollander, C., Luethy, J. D., Papathanasiou, M., Fargnoli, J., Holbrook, N. Mammalian genes coordinately regulated by growth arrest signals and DNAdamaging agents. *Mol. Cell. Biol.* 10: 4196–4203, 1989.

9. Gately, D. P., Sharma, A., Christen, R. D., Howell, S. B. Cisplatin and taxol activate different signal pathways regulating cellular injury-induced expression of GADD153. *British Journal of Cancer* 73: 18–23, 1996.

10. Luethy, J. D., Holbrook, N. J. Activation of the GADD153 promotor by genotoxic agents: a rapid and specific response to DNA damage. *Cancer Res.* 52: 5–10, 1992.

11. Gately, D. P., Jones, J. A., Christen, R., Barton, R., Los, G., Howell, S. B. Induction of growth arrest and DNA damage inducible gene gadd153 by cisplatin in vitro and in vivo. Br. *J. Cancer,* 70: 1102–1106, 1994.

12. Los, G., Barton, R. M., Nakata, B., Lee, L. K., van Veelen, L. R. and Howell, S. B., DNA damage and early-response genes as a tool to monitor tumor injury following chemotherapy. *Proceedings Amer. Assoc. Cancer Res.,* 34: 433, 1993.

13. Los, G., Barton, R., van Veelen, L., Woods, A., Vicario, D., Robbins, K. T., Howell, S. B. Association between DNA damage-inducible gene expression and tumor response. *Proc. Amer. Assoc. Cancer Res.* 35:550,1994.

14. Grenmaii, R., Burk, D., Virolainen, E., Buick, R. N., Church, J., Schwartz, D. R., and Carey, T. E. Clonogenic cell assay for anchorage-dependent squamous carcinoma cell lines using limiting dilution. *Int. J. Cancer,* 44: 131–136, 1989.

15. Nakata, B., Barton, R. M., Robbins, T. K., Howell, S. B., Los, G. Association between hsp60 mRNA levels and cisplatin resistance in human head and neck cancer cell lines. *Int. J. Oncology,* 6: 1425–1432, 1994.

16. Nakata B., Albright, K. D., Barton, R. M., Howell, S. B., Los, G. Synergistic interaction between cisplatin and tamoxifen and the delay of cisplatin resistance in head and neck carcinoma cell lines. *Cancer Chemother. Pharmacol.* 35: 511–518, 1995.

17. Robbins, R. T., Vicario, D., Seagen, S., Weisman, R., Pelliterri, P., Kerber, C., Orloff, L., Los, G., Howell, S. B. A targeted supradose cisplatin chemoradiation protocol for advanced head and neck cancer. *Am. J. Sur.* 168: 419–422, 1994.

18. Robbins, K. T., Stomiolo, A. M., Kerber, C., Vicario, D., Seagren, S., Shea, M., Hanchett, C., Los, G., Howell S. B. Phase I study of highly selective supradose cisplatin infusion for advanced head and neck cancer. *J. Clin. Oncol.* 12: 2113–2120, 1994.

19. Chomczynski, P., Sacchi, N. Single step method of RNA isolation by acid guanidium thiocyanatephenol-chloroform extraction. *Anal. Biochem.* 162: 156–159, 1987.

20. Horikoshi, T., Danenberg, K. D., Stadlbauuer, T. H. W., Volkenandt, M., Shea, L. C. C. Aigner, K., Gustavsson, B., Leichman, L., Frösing, R., Ray, M., Gibson, N. W., Spears, P. C., Danenberg, P. V. Quantitation of thymidylate synthase, dihydrofolate reductase, and DT-diaphorase gene expression in human tumors using the polymerase chain reaction. *Cancer Res.* 52: 108–116, 1992.

21. Sambrook, J., Fritch, E. F., Maniatis, T. Molecular cloning: A laboratory manual. Cold Spring Harbor Laboratory Press: Cold Spring Harbor, N.Y. 1989.

22. Davis, L. G., Bidner, M. D., Battey, J. F. Basic methods in molecular biology. Elsevier, N.Y., 1986.

23. Howell, S. B., Gately, D. P., Christen, R. D., Los, G. The cisplatin induced cellular injury response. In Platinum and other metal coordination compounds in cancer chemotherapy 2, H. M. Pinedo & J. H Schomagel (eds), Plenum Press, New York and London, page 269–282, 1996.

24. Jones, J. A., Gately, D. P., Barton, R. C., Albright, K. D., Christen, R. D., McClay, E. F., Los, G., Howell, S. B. Induction of GADD153 in human melanoma xenografts as an indicator of genotoxic injury. *Cellular Pharmacol.* 1: 233–237, 1994.

25. Fornace, A. J., Jackman, J., Hollander, M. C., Hoffman-Liebennan, B., Lieberman, D. H. Genotoxicstress-response genes and growth-arrest-genes. *Anal. N. Y. Acad. Sci.* 139–153, 1992.

26. Luethy, J. D., Holbrook, N. J. The pathway regulating gadd]53 induction in response to DNA damage is independent of protein kinase C of tyrosine kinases. *Cancer Res.* 54: 1902–1906, 1994.

27. Buscher, M., Ramsdorf, H. J., Litfin, M., Karin, M., Herrlich, P. Activation of c-fos gene by UV and phorbol ester: different signal transduction pathways covering the enhancer element. *Oncogene* 3: 301–311, 1988.

28. Devary, Y., Gottlieb, R. A., Lau, L. F., Karin. M. Rapid and preferential activation of the c-jun gene during the mammalian UV response. *Mol. Cell. Biol.,* 11: 2804–2811, 1991

29. Wang, A-Z, Ron, D. Stress-induced pliosphorylation and activation of the transcription factor CHOP (GADD153) byp38MAPkinase. *Science,* 1347–1349,1996.

30. Gasparini, G., Bevilacque, P., Bonoldi, E., Testolin, A., Galassi, A., Verderio, P., Boracchi, P., Guglielmi, R. B., Pezzella, F. Predictive and prognostic markers in a series of patients with head and neck squamous cell invasive carcinoma treated with concurrent chemoradiation therapy. *Clin. Cancer Res.* 1: 1375–1383, 1995.

31. Eymin, B., Dubrez, L., Attouche, M., Solary, E. Increased GADD153 Messenger RNA level is associated with apoptosis in human leukemia cells treated with etoposide. *Cancer Res.,* 57:686–695, 1997.

32. Los G, Benbatoul K, Gately DP, et al: Quantitation of GADD153 mRNA levels in human malignancies: a molecular marker for the tumor injury response. *Cancer Res.* In press: 1996.

33. de las Alas M, Christen R D, Kirmani S, et al: Correlation between tumor response and change in GADD153 mRNA level in human biopsies after paclitaxel treatment. Philadelphia, Pa. 1996.

34. Los G, Weisman R, Weiner D, et al: Identification of molecular markers reflecting the extent of injury induced in human tumors following treatment with chemotherapeutic agents. Washington D.C. 1996

What is claimed is:

1. A prognostic method for monitoring clinical response of a tumor to a chemotherapeutic agent comprising:
   a) obtaining a first biological sample from a patient having a tumor before treatment with said chemotherapeutic agent;
   b) obtaining a second biological sample from said patient after treatment with said chemotherapeutic agent; wherein said tumor is selected from the group consisting of endometrial adenocarcinoma, squamous cell cancer of the throat, squamous cell cancer of the lung, squamous cell cancer of the mandible, large cell lymphoma, colon cancer, and colorectal cancer;
   c) determining the level of mRNA for GADD153 in said first and said second samples; and
   d) comparing the levels of said GADD153 mRNA in said second sample with the level of GADD153 mRNA in said first sample; wherein the magnitude of increase in said GADD153 mRNA level in said second sample above the level of GADD153 mRNA in said first sample is indicative of the clinical response of said tumor to said chemotherapeutic agent, said clinical response comprising:
   i) tumor progression, wherein said increase is less than about 0.7 fold;
   ii) partial tumor regression, wherein said increase is greater than or equal to about 0.7 fold to less than or equal to about 2 fold; and
   iii) complete tumor regression, wherein said increase is greater than about 2 fold.

2. The prognostic method of claim 1, wherein said second biological sample is obtained at about 12 to about 48 hours after treatment with said chemotherapeutic agent.

3. The prognostic method of claim 2, wherein said second biological sample is obtained at about 18 to about 30 hours after treatment with said chemotherapeutic agent.

4. The prognostic method of claim 2, wherein said second biological sample is obtained at about 24 hours after treatment with said chemotherapeutic agent.

5. The prognostic method of claim 1, wherein the chemotherapeutic agent is paclitaxel, progesterone in combination with paclitaxel, or cisplatin.

* * * * *

UNITED STATES PATENT AND TRADEMARK OFFICE
CERTIFICATE OF CORRECTION

PATENT NO. : 6,447,997 B1  Page 1 of 1
DATED : September 10, 2002
INVENTOR(S) : Gerrit Los and Dennis P. Gately It is certified that error appears in the above-identified patent and that said Letters Patent is hereby corrected as shown below:

Column 7,
Line 6, please delete the word "to".

Column 8,
Line 53, "was" should read -- were --.

Column 11,
Line 57, "there" should read -- they --.

Column 12,
Line 13, please delete the space after "GADD153".

Column 15,
Line 57, "βACTIN" should read -- β-ACTIN --.

Column 16,
Line 54, please insert a space between "pp." and "425-440".

Column 17,
Line 4, please insert a space between "DNA" and "damaging".
Line 57, "Fr6sing" should read -- Frosing --.

Column 18,
Line 33, please insert a period after "1991".

Signed and Sealed this

Twenty-fourth Day of June, 2003

JAMES E. ROGAN
*Director of the United States Patent and Trademark Office*